(12) United States Patent
Wilson et al.

(10) Patent No.: US 6,371,956 B1
(45) Date of Patent: Apr. 16, 2002

(54) MONOPOLAR ELECTROSURGICAL END EFFECTORS

(75) Inventors: Jeffrey A. Wilson, Mendon, MA (US); John K. Danks, Delray Beach; Jim Young, Davie, both of FL (US)

(73) Assignee: Endoscopic Concepts, Inc., Delray Beach, FL (US)

( * ) Notice: Subject to any disclaimer, the term of this patent is extended or adjusted under 35 U.S.C. 154(b) by 0 days.

(21) Appl. No.: 09/376,170

(22) Filed: Aug. 17, 1999

Related U.S. Application Data (63) Continuation-in-part of application No. 08/942,133, filed on Oct. 1, 1997, now Pat. No. 5,954,720.
(60) Provisional application No. 60/029,405, filed on Oct. 28, 1996.

(51) Int. Cl.$^7$ ................................................. A61B 18/14
(52) U.S. Cl. .......................... 606/49; 606/46; 606/52; 606/170; 606/174
(58) Field of Search ..................... 606/45, 46, 48.52, 606/170, 174, 42

(56) References Cited

U.S. PATENT DOCUMENTS

| | | | | |
|---|---|---|---|---|
| 5,573,534 A | * | 11/1996 | Stone | 606/48 |
| 5,637,110 A | * | 6/1997 | Pennybacker et al. | 606/46 |
| 5,766,167 A | * | 6/1998 | Eggers et al. | 606/46 |
| 5,779,701 A | * | 7/1998 | McBrayer et al. | 606/46 |
| 6,039,733 A | * | 3/2000 | Buysse et al. | 606/40 |
| 6,113,596 A | * | 9/2000 | Hooven et al. | 606/42 |

* cited by examiner

Primary Examiner—Lee S. Cohen
(74) Attorney, Agent, or Firm—Miller & Martin LLP (57) ABSTRACT

A novel, monopolar, electrosurgical instrument is provided with one active and one non-active end effector. Current is passed through a conductive portion of one effector into tissue of a patient. The active blade may be partially or totally conductive. The non-active blade may be utilized to shield current from the active electrode effector.

22 Claims, 6 Drawing Sheets

MONOPOLAR ELECTROSURGICAL END EFFECTORS

This application claims priority as a continuation-in-part of U.S. patent application Ser. No. 08/942,133 filed Oct. 1, 1997, now U.S. Pat. No. 5,954,720, which claims the benefit of U.S. provisional application No. 60/029,405 filed Oct. 28, 1996.

BACKGROUND OF THE INVENTION

The present invention relates to endoscopic surgical instruments, and more particularly to instruments known as end effectors which may include cutters or scissors, graspers and dissectors which are useful in laparoscopic or endoscopic procedures. The surgical instruments made according to the present invention are monopolar.

The use of heat for the cauterization of bleeding wounds dates back for centuries. More recently, the use of radio frequency (RF) electrical current traveling through a portion of the body has been widely used to stop bleeding. The RF energy cauterizes the blood by heating the blood proteins to a temperature where those proteins congeal similarly to the process involved in the cooking of egg whites. RF energy is preferred because its frequency is above that which could otherwise cause neuromuscular stimulation. The most frequently used modes of RF cauterization are monopolar and bipolar coagulation.

In monopolar coagulation, an active electrode is applied to a bleeding site and electrical current flows from the electrode through the patient's body to a return electrode which may be a conductive plate in electrical contact with a large surface area of the patient's body such as the buttocks or thigh. One technique in which the monopolar mode may be employed involves fulguration which is the use of a spark or arc from the active electrode to the tissue.

Bipolar devices include both the active and return electrodes. Thus the electrical current flows down the surgical instrument to the active electrode and typically crosses a space on the order of millimeters, or shorter, to the return electrode and returns through the surgical device.

Endoscopic surgical instruments, such as the monopolar electrosurgical end effectors, are often used in laparoscopic surgery, which is most commonly employed for cholecystectomies (gall bladder surgeries), hysterectomies, appendectomies, and hernia repair. These surgeries are generally initiated with the introduction of a Veress needle into the patient's abdominal cavity. The Veress needle has a stylet which permits the introduction of gas into the abdominal cavity. After the Veress needle is properly inserted, it is connected to a gas source and the abdominal cavity is insufflated to an approximate abdominal pressure of 15 mm Hg. By insufflating the abdominal cavity, a pneumoperitoneum is created separating the wall of the body cavity from the internal organs. A surgical trocar is then used to puncture the body cavity. The piercing tip or obturator of the trocar is inserted through the cannula or sheath and the cannula partially enters the body cavity through the incision made by the trocar. The obturator can then be removed from the cannula and an elongated endoscope or camera may be inserted through the cannula to view the body cavity, or surgical instruments such as monopolar electrosurgical end effectors according to the present invention, may be inserted to perform the desired procedure.

Frequently an operation using trocars will require three or four punctures so that separate cannulas are available for the variety of surgical instruments which may be required to complete a particular procedure. Additionally, electrosurgical instruments, such as this design for monopolar end effectors, may be utilized in open surgery techniques as well.

Other techniques for coagulation have a variety of shortcomings. While non-contact positioning of a laser may be useful in some instances, the laser has no way of holding a bleeding vessel and is not used on large bleeders. Laser based cauterization instruments remain expensive and unsuitable for tissue dissection techniques other than cauterization, such as blunt dissection or sharp dissection. Laser cauterization instruments suffer from the additional shortcomings of difficulty controlling the depth of penetration of the laser energy and that non-contact positioning of a laser can permit the laser beam to reflect off of other instruments and cause damage to surrounding tissue.

Monopolar end effectors may be useful in particular applications in which bi-polar instruments are not a preferred option due to technical restraints. Additionally, some of the prior art monopolar instruments may have predictability problems in current flow due to the use of two conducting blades acting as one electrode in conjunction with a separate electrode. Furthermore, the operator may be limited by particular end effector designs which do not allow for a more precise channeling of RF energy.

Presently, monopolar effector designs, especially monopolar scissors, utilize a pair of relatively large metal blades, at least one of which also functions as an electrode. Even if only one blade were utilized as an electrode during an energized procedure, the other blade is also active and may act as a conductor and attract or conduct current to tissues. Current will generally follow the path of least resistance. The presence of a second active blade in close proximity to an energized electrode provides an attractive current path. This is not a desirous result for a user as this effectively increases the surface area of the active electrode. It is believed that the larger the exposed area of the active electrode, the larger chance that a surgeon may inadvertently conduct current into unintended portions of tissue. Conducting current into unintended tissue may damage tissue and result in collateral damage.

The present invention incorporates two blades: (1) an active blade and (2) an insulated and/or inactive blade. With both scissors blades closed, the inactive blade may be used as a shield while the active blade is utilized as an electrode. The insulated blade may protect tissue including organs when using the active electrode. The inactive blade may, or may not, contact tissue during the use of an active electrode.

Monopolar effectors have been found to be effective at a technique known as spray fulguration which allows for current to be jumped to the tissue without contact of the effector with the tissue. Other techniques useful to operators may, or may not, involve contact of the monopolar electrode with a particular tissue. The invention described herein overcomes common monopolar end effector shortcomings and may effectively reduce the number of surgical instruments required for a given procedure.

SUMMARY OF THE INVENTION

It is therefore an object of the invention to provide an improved surgical instrument with monopolar end effectors.

It is an additional object of the invention to provide an instrument having monopolar end effectors wherein one end effector has an active conducting portion and the other effector is inactive.

It is a further object to pass current through the conducting portion of the first end effector to effect coagulation caused by the RF energy at a location desired by the operator.

It is yet a further object of the invention to provide a monopolar instrument which utilizes RF energy more precisely to cauterize a particular tissue portion and thereby minimize damage to other tissue.

Another object of the invention is to provide the ability to energize and de-energize the RF energy at the electrode.

Another object of the invention is to provide a conductive portion of a blade of an end effector and a second non-active blade.

It is still a further object of the invention to allow the operator to utilize the effectors to dissect spread, or move tissue independent of coagulation procedures.

Still another object is the minimization of lateral damage to surrounding tissue as current is conducted from a single blade to the tissue.

Additionally, an advantage of the invention is the ability to use the non-active blade to protect particular tissue from inadvertent exposure to coagulation current while utilizing the active electrode.

These and other objects of the invention are accomplished by the utilization of one blade having a current conduit connected to a conductive portion. This active blade may be utilized to cut tissue in conjunction with a second non-active blade.

DESCRIPTION OF THE PREFERRED EMBODIMENT

Figure 1:
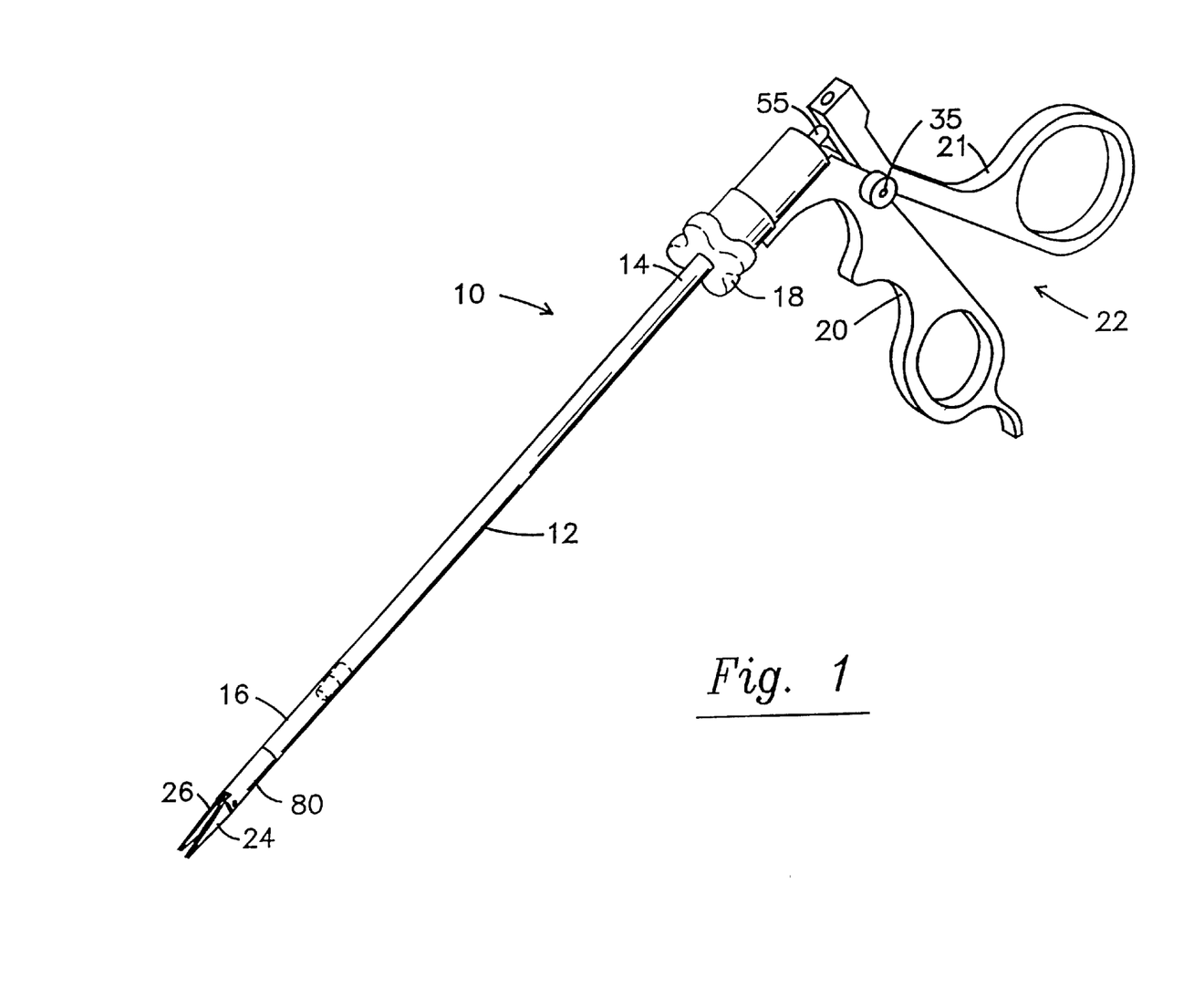
FIG. 1 is a perspective view of an endoscopic electrosurgical scissors constructed in accordance with the present invention.

Referring to FIG. 1, there is indicated generally by numeral 10 a monopolar electrosurgical scissors for endoscopic surgery constructed having end effectors in accordance with the present invention. It will be understood that the principles of the present invention are equally suitable for use in other monopolar end effector instruments such as graspers and dissectors.

Although many types of monopolar effectors are known in the art, this description will be directed at a single scissor type for purpose of explanation. It should be obvious to one skilled in the art that any monopolar effector design, especially monopolar scissors having end effectors as described herein, are contemplated by this invention.

The scissors 10 are seen to typically include an elongated tubular barrel 12 having a proximal end 14 a distal end 16, and with a lumen extending there between. The outer diameter of the barrel 12 is sufficiently small to be passed through the working lumen of a trocar cannula. Tubular barrel 12 is preferably an insulated metal tube, as by Teflon coating, or a rigid plastic tube. Mounted on the proximal end 14 of the tubular barrel 12 of the monopolar scissors 10 is a knob 18 which facilitates rotation of the tubular barrel 12 and connected end effectors. The tubular barrel 12 and knob 18 are mounted to the stationary portion 20 of an actuator such as handle assembly 22. Manipulation of moveable scissors handle 21 relative to stationary handle section 20 manipulates push rod connector 55 and push rod 50 (illustrated in FIG. 13) which is internal to push rod connector 55 and tubular barrel 12 and in linked communication with end effectors such as blades 24 and 26, which are thereby caused to move in scissors-like action relative to one another. The scissors-like action may be utilized to dissect, spread, or move tissue without utilizing RF energy.

Figure 6A:
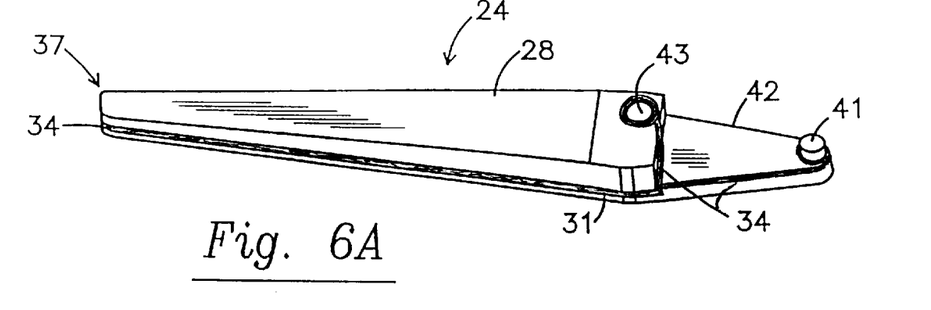
FIG. 6A is a perspective view of a first blade portion according to the present invention.

Referring to FIG. 6A, an enlarged view of a first end effector, such as scissors blade 24 is provided. In a presently preferred embodiment, a first scissors blade 24 is comprised of a nonconductive blade blank 28 which is preferably constructed of a ceramic material such as Zirconia, Mullite, or Alumina available from Coors Ceramics Company, Inc., but which also might be suitably constructed of rigid plastic or insulated metal. Alternatively the first scissors blade 24 may be comprised of a conductive blank with a nonconductive material, typically ceramic, facing the second blade 26, though the cutting edge may still be metal.

At the proximal end 41 of the first blade 24 is a post 41, a function of which will be explained in connection with cam socket 70 shown in FIG. 12. Proceeding from the post 41 or preferably a surface area on the same side of proximal end 42 of first blade 24, perhaps adjacent to aperture 43, is a conductor 34 which proceeds through groove 31 down at least a portion of the end effector, such as blade 24. Preferably, the conductor 34 will proceed directly to the proximal portion of a conductive cutting edge 29 rather than as illustrated to the distal end 37 of the end effector and thereby be connected to an exterior portion of the blade 24 such as to the cutting side of the first blade 24 as by connection 36, shown in FIG. 6B. Preferably the conductor 34 is insulated as it proceeds along the end effector to connection 36 to prevent inadvertent RF current discharges into tissue. The connection 36 connects conductor 34 to an exposed conductive portion 30 (shown in FIG. 6B). In this embodiment, conductive portion is located on cutting edge 29.

Figure 6B:
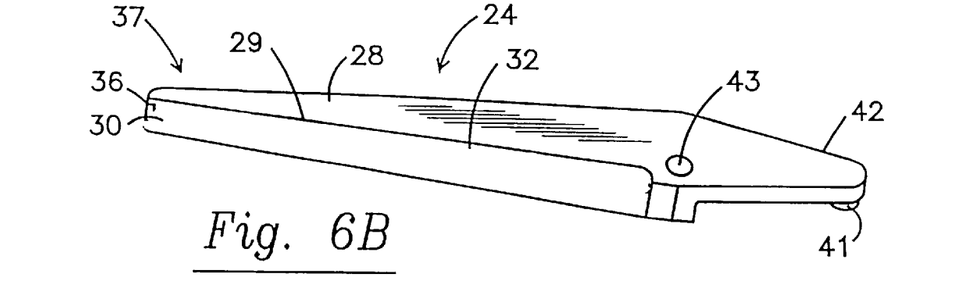
FIG. 6B is a reverse angle view of the first blade portion of FIG. 6A.

In an embodiment provided for purpose of explanation, the conductive portion 30 is located on an exterior surface near a cutting side of the blade 24. However, multiple or alternative conductive portions 30 or surfaces of a single blade 24 may be found effective for some applications. One or more may be placed on any exterior surface of blades such as on the top, bottom, or other sides of the blade 24. Multiple conductive portions 30, if utilized, may then have means to select therebetween for an operator to choose which conductive portion 30 or portions 30 to energize. It is possible that the entire first blade 24 be a conductive portion 30 constructed of a conducting material such as metal, as an alloy of steel, but it need not be limited in such regard. Any known conductive material may be utilized for conductive portion 30.

Figure 6C:
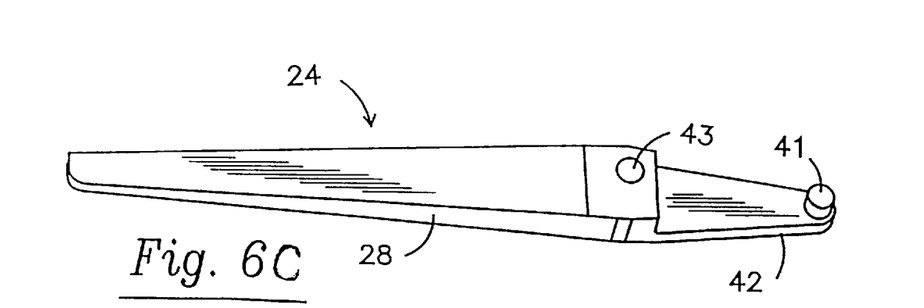
FIG. 6C is a perspective view of an alternatively preferred embodiment of a first blade.

Accordingly, FIG. 6C shows a standard metal scissors blade 24 also having a proximal section 42 with post 41 which could be utilized as a first blade 24. Blade 24 may have an aperture 43 and may be manufactured from a traditional metal end effector blank 28. It will be understood that the end effectors may have a variety of shapes and, in particular end effectors for scissors, may have a curved profile. The first blade 24 may have insulated portions to assist in directing current to specific conductive portions 30.

Figure 7:
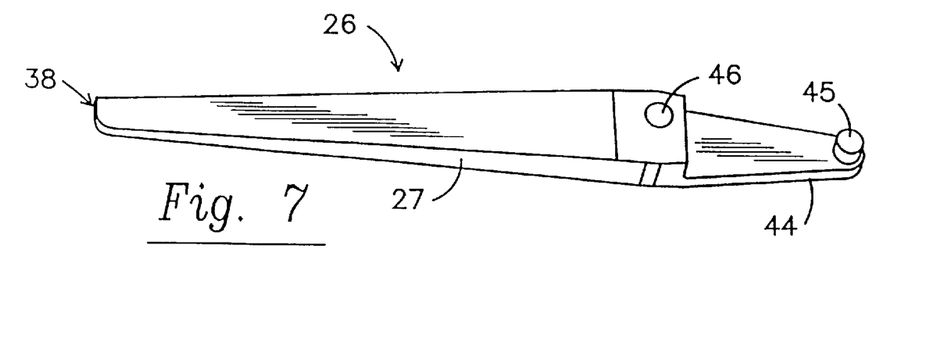
FIG. 7 is a perspective view of a second blade portion according to the present invention.

FIG. 7 shows a second blade 26. The second blade 26 is non-active which implies that the blade does not conduct electricity across its entire cross section. Typically, second blade 26 is constructed of a non-conductive material such as ceramic. Alternatively, the non-active blade may be an insulated metal blade, or a non-active metal blade. A typical construction involves the use of a metal blank with a ceramic surface on all areas that contact the first blade 24. The second blade 26 is shown having a proximal section 44 with post 45. The second blade 26 also has an aperture 46 which corresponds to the aperture 43 on the first blade 24. It will be understood that the second blade may have a variety of shapes and need not be symmetrical in shape with the first blade 24.

Figure 2:
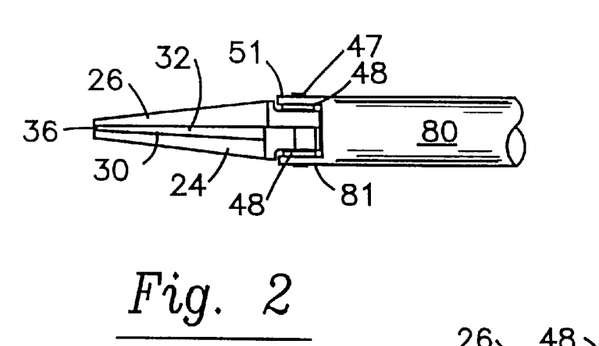
FIG. 2 is a top view of the distal end of a portion of the scissors of FIG. 1.

FIGS. 2 through 5 show different views of second blade 26 and a first blade 24 mounted in clevis section 80. FIG. 2 is a top view showing connecting rivet 47 holding pressure washers 48, second blade 26, and first blade 24, in alignment between clevis wings 81 so that blades 24 and 26 may move in pivotable relation to each other. It will be understood that a single pressure washer 48 may be sufficient. Shown on first blade 24 is exposed conductive portion 30 located on cutting edge 29.

Figure 3:
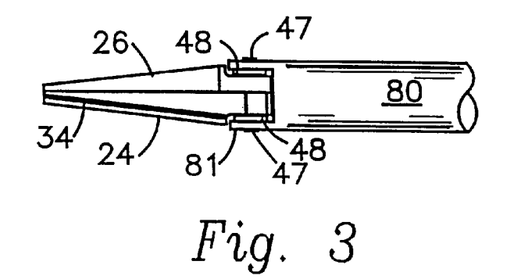
FIG. 3 is a bottom view of the distal end portion of the scissors of FIG. 1.

In the bottom plan view of FIG. 3, a conductor 34 is shown. This conductor 34 connects via connection 36 to the exposed conductive portion 30 (shown in FIG. 2). While it is anticipated that the conductor 34 may be plated or press fit into groove 31 and thereafter covered with an insulating resin, it may also be possible to cast the blade 24 from ceramic or plastic with conductor 34 embedded within the blade blank 28. In the preferred embodiment, it is contemplated that the conductor will proceed directly to the proximal portion of conductor 30, relatively near the connecting rivet 47, rather than around the distal end 37 of the blade 24. Furthermore, the conductive portion 30 need not necessarily be located near the cutting edge of the blade. The conductive portion 30 may alternatively be located on the top, bottom, or non-working side of the blade 24, to permit cauterization separate from the end effector action.

Figure 4:
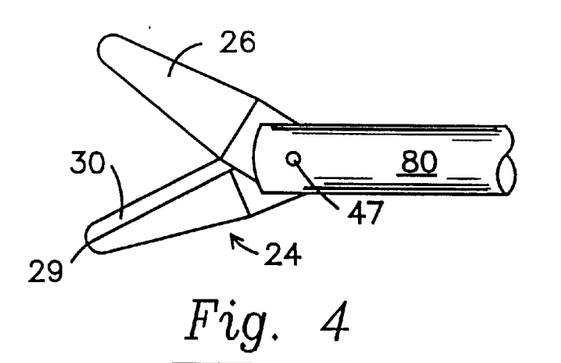
FIG. 4 is a side plan view of the distal end of a portion of the scissors of FIG. 1 in their open position.

FIG. 4 is a left side view showing scissors blade 26 and 24 in their open position. With the cutting side of first blade 24 exposed, the conductive portion 30 is shown.

Figure 5:
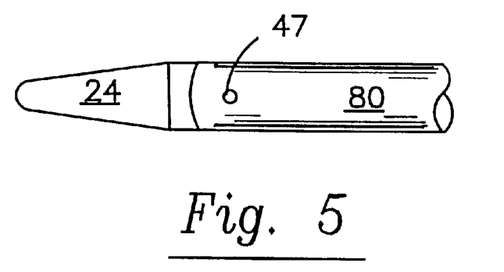
FIG. 5 is a side plan view opposite FIG. 4 of the distal end of a portion of the scissors of FIG. 1 in their closed position.

FIG. 5 shows a right side view with blades 24 and 26 in their closed position so that only first blade 24 is apparent. It will be understood that while the blades 24, 26 shown in these illustrations have a linear profile when observed from the top as in FIG. 2, the blade profiles could alternatively be arcuate if preferred. Alternatively, one of the blades 24, 26 may be slightly arcuate and the other linear. The blades 24, 26 also need not be symmetric.

These end effectors may be utilized on a variety of instruments, one scissor apparatus is described below to illustrate an effective manner of operating these end effectors.

Figures 12, 14:
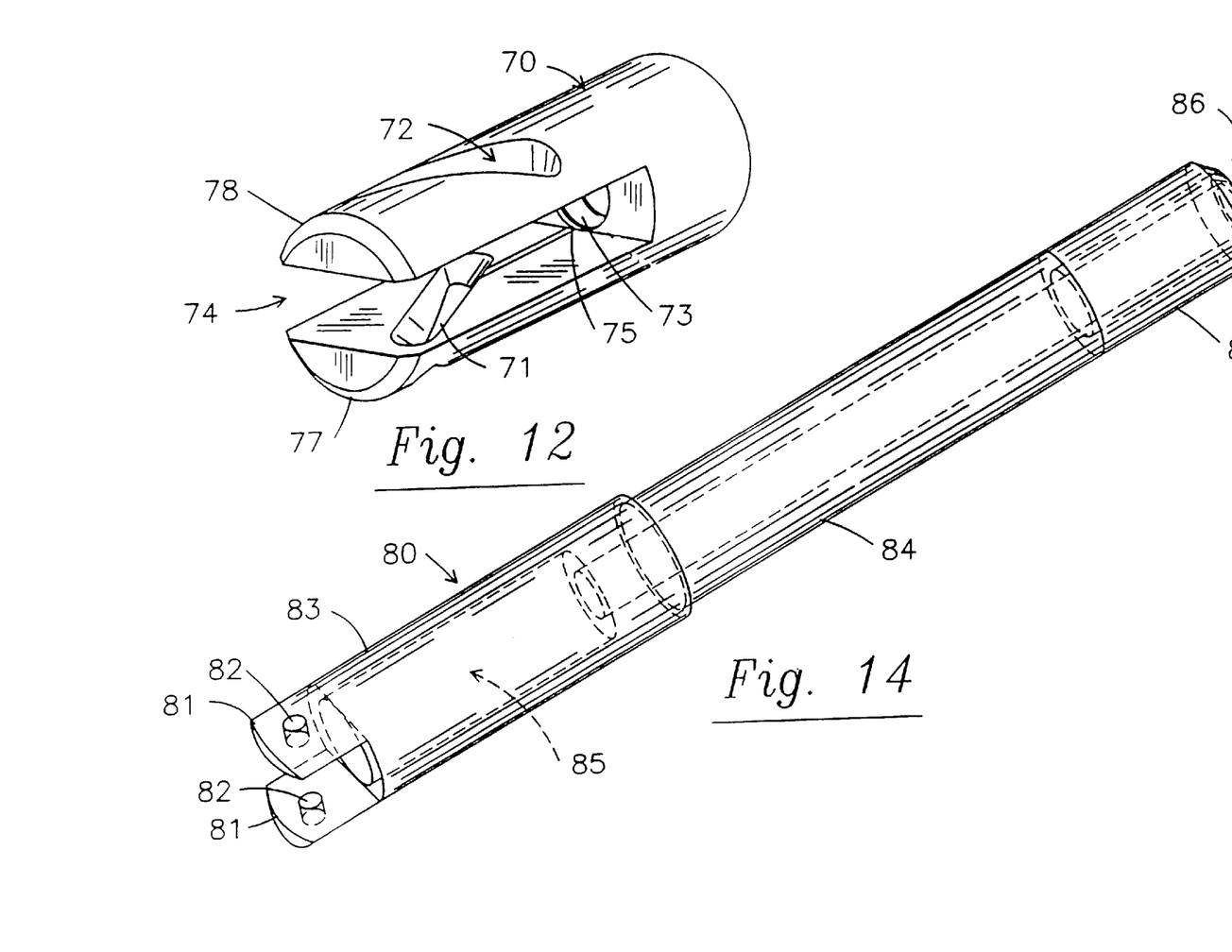
FIG. 12 is a perspective view of a cam part according to the present invention.
FIG. 14 is a perspective view of a clevis section used with monopolar end effectors made according to the present invention.

Turning now to the assembly of monopolar end effectors, first blade 24 and second blade 26 are mounted in cam socket 70 (shown in FIG. 12). First side 77 and opposed side 78 of cam socket 70 define a channel 74 at the distal end of cam socket 70. At the proximal end of cam socket 70 is aperture 73 which contains a connection strip 75 for connecting with an electrical connection 52, on push rod 50 shown in FIG. 13. It will be understood that the illustrated connection strip 75 is specifically adapted to conduct current to the post 41 of the first blade 24 and through the connector 34 to the conductive portion 30 of the blade through tissue and to another electrode having opposite polarity of the polarity of the current at the active conductor portion 30. It may also be preferred to conduct current to other surfaces on the blade 24 such as adjacent to aperture 43 to conduct current to the conductive portion 30.

In order to secure the blades with their protruding posts 41, 45, the cam socket 70 may be made of a flexible or elastomeric material such as a plastic polymer such as polyurethane that will permit first side portion 70 and second side portion 78 to be bent apart from each other when blades 24, 26 are inserted. Alternatively, the cam socket 70 may be made of rigid material and the blades 24, 26 inserted in a staggered manner and then aligned at the pivot point represented by apertures 43, 46. The post 41 on first blade 24 is received in groove 71 on the first side 77 of cam socket 70, while post 45 on second 26 is received in groove 72 on the opposed side 78.

Attached to cam socket 70 by means of chemical, dielectric, or other appropriate bonding, is a connection strip 75 to first cam socket side 77 so that it may interface with the conductor 34 on the non-cutting side of first blade 24.

When blades 24, 26 are mounted in cam socket 70, push rod 50 (shown in FIG. 13) is inserted into aperture 73 so that connector 52 is in contact with connective strip 75. Although push rod 50 may be a relatively small diameter tube containing at least one insulated wire, it is preferably rigid plastic formed with an internal conductor 51 proceeding from connector 52 internal of push rod 50 to proximal end 53. The assembled blade 24, 26, cam socket 70, and push rod 50 assembly is then inserted between opposed wing sections 81 of clevis section 80. The push rod proceeds through lumen 86 of clevis section 80, while the cam socket 70 is received within chamber 85 of the clevis section 80, and ends 37, 38 of blades 24, 26 are protruding. Apertures 43, 46 on blades 24, 26 respectively (shown in FIGS. 6–7), are aligned with apertures 82 on the clevis section 80, optionally with one or more spring washers 48 (shown in FIGS. 2 and 3) and connected by rivet 47 (shown in FIGS. 2 through 5). If desired, this entire assembly of blades, clevis section, cam socket, and push rod may be disposable.

Figures 10, 11, 13:
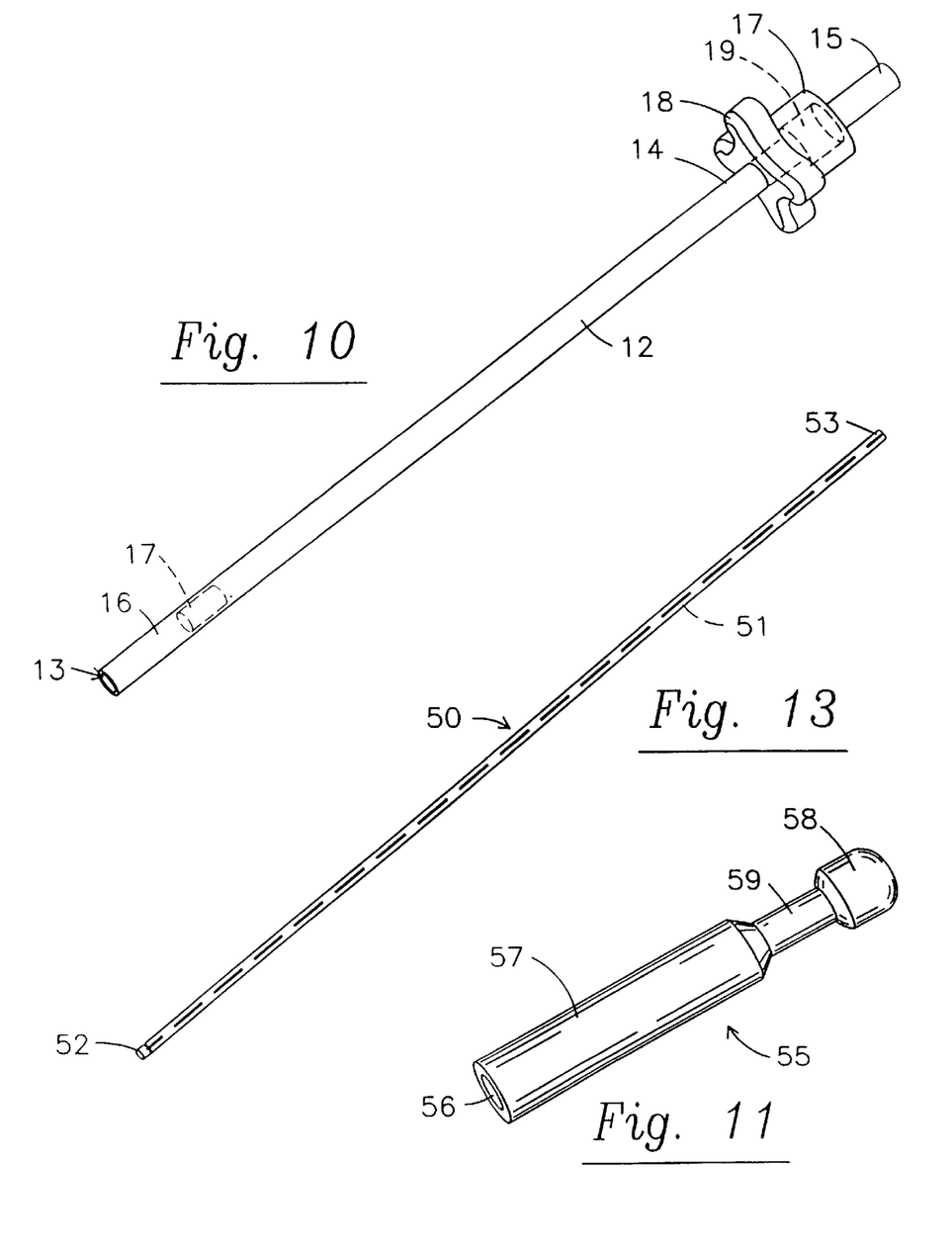
FIG. 10 is a perspective view of an elongated tubular barrel for end effectors having a grasping knob to facilitate rotation.
FIG. 11 is a perspective view of a push rod connector for use in an electrosurgical end effector.
FIG. 13 is a side view of an internal push rod adapted to transmit current or wire connectors through the tubular barrel of an electrosurgical end effector.

Turning now to FIG. 10, the proximal end of push rod 53 is threaded through lumen 13 beginning at the distal end 16 of tubular barrel 12 until it projects at the proximal end 15. When so positioned, the proximal end 87 of clevis section 80 is fixed in mounting section 17 internal to the tubular barrel. Mounting section 17 and proximal clevis section 87 may be press fitted or preferably have mating threads for secure positioning. Relatively narrower section 84 of clevis section 80 (shown in FIG. 14) is received within the proximal end 16 of tubular barrel 12 while relatively wider section 83 of clevis section 80 protrudes from barrel 12.

Figure 8:
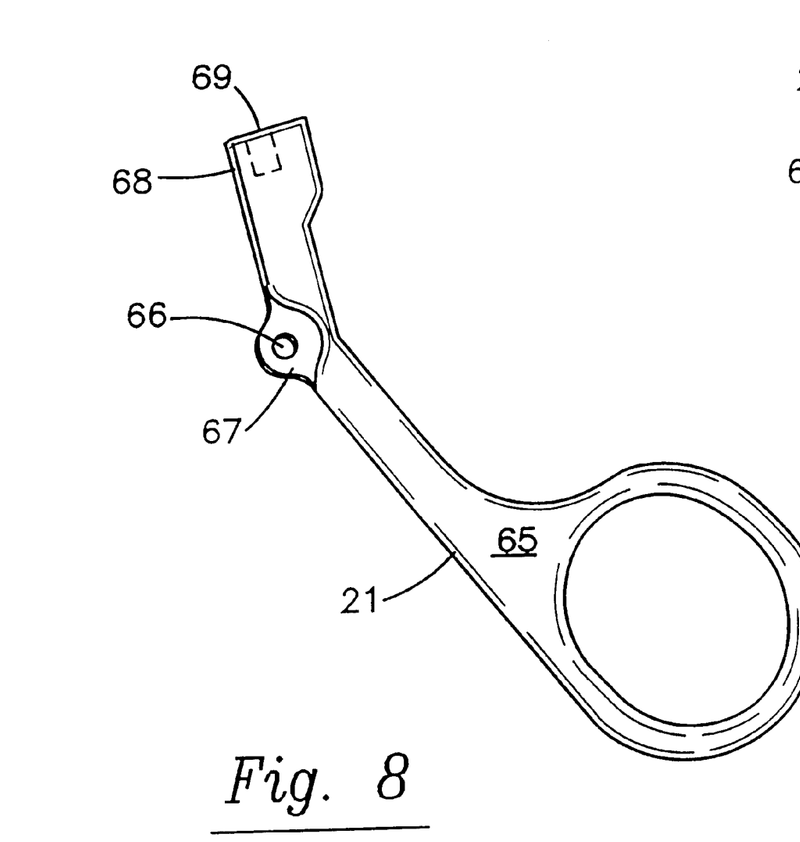
FIG. 8 is a side view of a moveable handle portion for a monopolar end effector.
Figure 9:
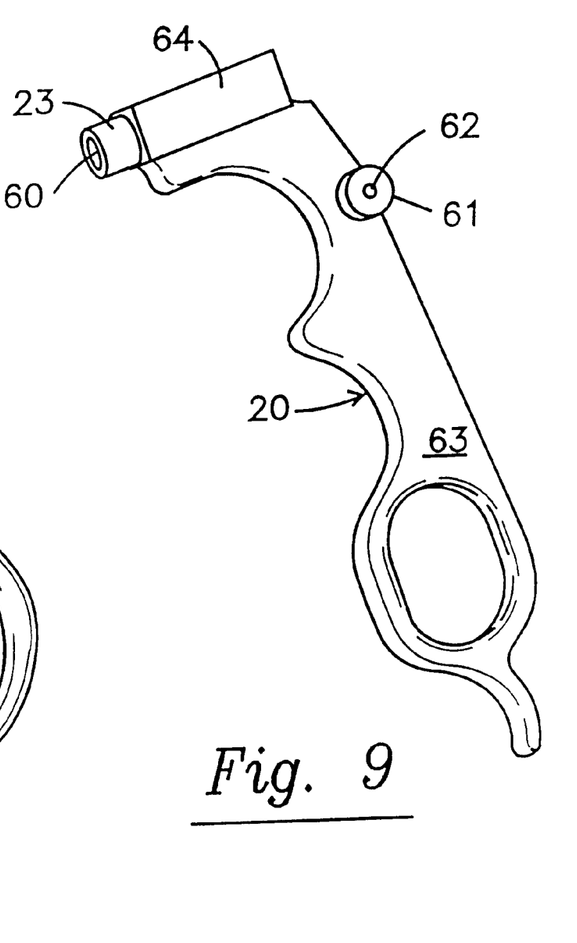
FIG. 9 is a side view of a stationary handle portion for a monopolar end effector.

The next assembly step is for proximal end 15 of tubular barrel 12 to be mounted in aperture 60 of stationary scissors handle 20 (shown in FIG. 9). Protruding fitting segment 23 on stationary handle 20 is in turn received within chamber 19 of tubular barrel assembly 12. The proximal end 53 of push rod 50 protrudes through aperture 60 of stationary handle section 20. Stationary handle 20 has an upper section 64 and a lower handle 63. Also shown is a structure for pivotable attachment with movable handle 21 (shown in FIG. 8) consisting of a clevis like arrangement of two raised circular sections 61 defining between them a gap to receive protruding section 67 on movable handle 21 and each having a threaded aperture 62.

Prior to assembling movable handle section 21 (shown in FIG. 9) with stationary handle 20, push rod connector 55 is first mounted into the circle and slot configuration 68 of the movable handle 21. Bulbous portion 58 of push rod connector 55 (shown in FIG. 11) is inserted through the circular section of opening 68 until the entire bulbous section 58 is internal of movable handle 21 and thereafter neck 59 of push rod connector 55 is slid into the slot section (having a width less than the diameter of bulbous head 58) of opening 68 so that the bulbous head 58 will not pull free. When so positioned, the lumen 56 proceeding through push rod connector 55 is in alignment with an internal electrical connector plug in communication with external electrical connector plug 69 at the upper end of movable handle 21.

It should also be noted that aperture 66 of movable handle 21 is sized somewhat larger than aperture 62 on stationary handle 20. The two handle sections 21 and 20 are joined at two points. First, the proximal end 53 of push rod 50 passing through the upper portion 64 of stationary handle section 20 is received through aperture 56 of push rod connector 55 so that it connects through opening 68 into movable handle 21. The proximal end 53 of push rod 50 is thereby placed in electrical connection with tube connector socket 69. The handle sections 20, 21 are also joined by positioning protrusion 67 of moveable handle section 21 in between the clevis like structures 61 on stationary handle 20 and inserting a screw through threaded apertures 62, said screw threads not engaging with the movable scissors handle 21 because of the relatively larger size of aperture 66. This permits free pivoting of the handle sections relative to one another, thereby effecting the pushing or retraction of push end 50 relative to the end effectors.

To utilize the monopolar end effectors according to the present invention, plug 69 is connected with appropriate monopolar power source. In use, the positive RF energy proceeds from plug 69 through central electrical connector 51 of push rod 50 to connector 52 at the distal end thereof, and to connective strip 75 of scissors cam socket 70. From connector 70, a current is received by connector 34 on first blade 24. When energized, RF current proceeds along conductor 34 to communicate with the exposed conductive portion 30. When exposed conductive strip 30 is energized, current will flow from it to a separate second electrode. The separate electrode (not shown) is generally placed in electrical contact with an exterior portion of the patient's body.

When it is desired to cauterize tissue, RF voltage is applied to the electrosurgical scissors thereby making the exposed conductive portion 30 of the first blade 24 the active electrode. When the scissors are in proximity with tissue, current flows from a part of the conductive portion 30 through the tissue to the separate second electrode. One technique involves jumping current to the tissue without contact. This spray fulguration technique may be performed more precisely with a monopolar device having only a defined conductive area than with other monopolar devices. Other cauterization techniques may also be employed by users.

The scissors may, or may not, be closed when the conductive portion 30 is an active electrode. If the scissors are closed, the non-active blade may protect particular tissue from current. The non-active blade may also be utilized to protect particular tissue from current when the instrument is in an open, or partially open, position.

Limiting current flow to a single effector to the tissue may allow the operator to better protect particular tissue from lateral damage from stray current from other portions of active blades.

When it is not desired to cauterize tissue, RF energy to the scissors may be switched off thus allowing the scissors to blunt dissect and spread tissue independent of coagulation.

The present invention promotes the precise use of RF energy by containing the flow of positively charged energy particles through a well defined positive electrode 30 at a precise location to be chosen by the operator. Some of the current is absorbed to heat the tissue and the remaining positive energy is pulled into a separate negative electrode, thus minimizing the escape of energy from the instrument into surrounding tissues. The novel design focuses the RF energy in an effort to reduce the amount of energy required to produce coagulation at the cutting site and to effectively remove the residual energy from the patient's body without affecting other tissues. Lower energy settings may result in less char and buildup in the instrument in addition to reducing the likelihood that the energy will affect other tissue or organs.

Electrical connections are possible that still permit the rotation of barrel 12 upon turning knob 18 without causing a loss of current to the end effectors. The novel cam socket 70 of the present invention obviates the necessity for placing a slot in first blade blank 28 effect the scissors action. Instead, both blanks 27, are only weakened by a single aperture 43, 46. If multiple holes or substantial slots were cut in blanks 28, it would substantially increase the risk of mechanical failure of the blanks especially if constructed of a ceramic material.

The specific embodiments described are provided t by way of explanation rather than limitation and variations that do not depart from the spirit of the invention are intended to be covered by the appended claims.

What is claimed is:

1. A monopolar surgical instrument comprising:
 first and second interfacing end effectors wherein at least one of said first and second end effectors is pivotable relative to the other;
 said first end effector having a side interfacing with the second end effector, and a cutting edge on said interfacing side;
 said second end effector having a side interfacing with the first end effector, and a cutting edge on said interfacing side; and
 wherein said first end effector is in electrical communication with a monopolar power source and has an electrically conductive portion located on a surface, and said second end effector is not electrically active and is non-conductive on substantially all exposed surfaces.

2. The monopolar instrument of claim 1 wherein said first and second end effectors are pivotably mounted in a clevis section.

3. The monopolar instrument of claim 2 wherein said first and second end effectors each have an intermediate aperture and the clevis section has a distal end with two opposed wings and a pin interconnecting said opposed wings and passing through the intermediate apertures of the first and second end effectors.

4. The monopolar instrument of claim 1 wherein the first end effector has a proximal end, a distal effector end, an interfacing side and an opposed side with a post protruding from the opposed side of the proximal end; and the second effector has a proximal end, a distal effector end, an interfacing side, and an opposed side with a post protruding from the opposed side of the proximal end.

5. The monopolar instrument of claim 1 wherein the conductive portion of the first end effector is a substantial portion of the first end effector.

6. A monopolar surgical instrument comprising:

first and second interfacing end effectors wherein at least one of said first and second end effectors is pivotable relative to the other, said first end effector having a proximal end, a distal effector end, an interfacing side, and an opposed side with a post protruding from the opposed side; said second end effector having a proximal end, a distal effector end, an interfacing side, and an opposed side with a post protruding from the opposed side; and a cam socket having a proximal end and a distal end, said distal end having a first side portion with a groove defined therein to receive the post protruding from the first end effector, and having a second side portion with a groove defined therein to receive the post protruding from the second end effector, and wherein said first end effector has a conductive portion located on a surface which is electrically conductive, and said second end effector is not electrically active.

7. The monopolar instrument of claim 6 wherein said cam socket is received within a clevis section and said first and second end effectors each have an intermediate aperture and the clevis section has a distal end with two opposed wings and a pin interconnecting said opposed wings and passing through the intermediate apertures of the first and second end effectors.

8. The monopolar instrument of claim 7 wherein the clevis section has an electrical connector in contact with the electrically conductive portion of the first effector.

9. The monopolar instrument of claim 8 wherein said electrical connection is electrically connected to an active terminal of an RF power supply.

10. A monopolar surgical instrument comprising:

(a) an actuator;

(b) a tubular section having a proximal end connected to the actuator and a distal end;

(c) a clevis section connected to the distal end of the tubular section;

(d) a push rod extending through the tubular section having a proximal end and a distal end;

(e) a cam socket comprising a distal end having a first side portion with a groove defined therein and a second side portion with a groove defined therein and wherein said first and second side portions define a channel;

(f) a first end effector having:

(i) a proximal end and a distal end and an interfacing side and an opposite opposed side and wherein a post protrudes from the proximal end of said opposed side, said post being received in the groove defined in the second side portion of the cam socket;

(ii) an aperture proceeding from the interfacing side to the opposed side intermediate the proximal and distal ends;

(iii) a electrical conductor;

(iv) an electrical connection in contact with said electrical conductor;

(v) an electrode in contact with said electrical connection; and (g) a second non-active end effector having a proximal end and a distal end and an interfacing side and an opposite opposed side and wherein a post protrudes from said opposed side proximal end which is received in the groove defined in the first side portion of the cam socket;

(h) the clevis section having a proximal end encompassing said cam socket and being connected to the distal end of the tubular section and having a distal end defining two opposed clevis wings each having an aligned aperture, said clevis section further comprising a pin received through the aperture of a first clevis wing, the intermediate aperture of the first end effector, an intermediate aperture of the second end effector, and the aperture of the opposed clevis wing, thereby making said first and second end effectors pivotable relative to the other.

11. The monopolar instrument of claim 10 wherein the second end effector comprises a working surface on the interfacing side that engages with the first end effector when the end effectors are pivoted.

12. The monopolar instrument of claim 11 wherein the working surface is a cutting edge.

13. The monopolar instrument of claim 11 wherein the second end effector is non-conductive where it contacts and comes into close proximity to the first end effector.

14. The monopolar instrument of claim 13 wherein the portions of the second end effector that contact and come into close proximity to the first end effector are fabricated of non-conductive ceramic material.

15. A method of surgically cauterizing tissue of a patient comprising the steps of:

(a) obtaining a monopolar surgical instrument having a handle with an actuator, first end effector having an interfacing side with a cutting edge, and a second end effector having and interfacing side with a cutting edge, wherein (i) at least one of said first and second end effectors is pivotable relative to the other in response to the actuator;

(ii) said first end effector has an exposed electrode and is capable of electrical connection to a RF power supply, (iii) said second end effector has a proximal end, a distal effector end, an interfacing side with a working surface, an opposed side and is not electrically active and has no effective conductive surfaces; and (iv) the working surface of the second end effector contacts the first end effector at least when actuated;

(b) placing a separate electrode in electrical contact with the patient;

(c) electrically connecting the active terminal of an RF power supply to the exposed electrode of the instrument; and (d) placing the exposed electrode in sufficient proximity to the tissue that RF energy from the power supply proceeds between the exposed electrode and the separate electrode and into the tissue thereby cauterizing tissue proximal to the exposed electrode upon electrical connection of the RF power supply to said exposed electrode.

16. The monopolar instrument of claim 15 wherein the second end effector is insulated from the electrode of the first end effector.

17. A monopolar surgical instrument comprising:

a first end effector having a proximal end, a distal end, an interfacing side having a first cutting surface, an opposite side, and an exposed electrode connected to a monopolar power source, said first cutting surface being interfacing and pivotable relative to a second end effector having a second cutting surface, wherein said second end effectors is selected from the group consisting of non-conductive effectors and fully electrically insulated end effectors.

18. The monopolar instrument of claim 17 wherein the exposed electrode is on the interfacing side and said first end effector further comprises a non-conductive blank, a conductor beginning toward the proximal end and connecting to the exposed electrode on the interfacing side.

19. The monopolar instrument of claim 17 wherein the second end effector is insulated from the exposed electrode of the first end effector.

20. The monopolar instrument of claim 19 wherein the second end effector is insulated by ceramic material.

21. The monopolar instrument of claim 17 wherein the second end effector is comprised of a ceramic interfacing side.

22. A monopolar surgical instrument comprising first and second cutting means for cutting tissue there between wherein:

said first cutting means has a side interfacing with the second cutting means and an electrode on said interfacing side in electrical communication with a monopolar power source; and said second cutting means is not electrically active and has a non-conductive outer surface upon substantially all exposed surface portions.

* * * * *